United States Patent
Dubief et al.

(10) Patent No.: US 7,176,170 B2
(45) Date of Patent: Feb. 13, 2007

(54) SHAMPOO COMPRISING AT LEAST ONE SILICONE AND AT LEAST ONE ANIONIC OR NONIONIC, AMPHIPHILIC LINEAR BLOCK COPOLYMER

(75) Inventors: Claude Dubief, Le Chesnay (FR); Serge Restle, Saint Prix (FR); Franck Giroud, Clichy (FR)

(73) Assignee: L'Oreal, Paris (FR)

( * ) Notice: Subject to any disclaimer, the term of this patent is extended or adjusted under 35 U.S.C. 154(b) by 60 days.

(21) Appl. No.: 10/449,721

(22) Filed: Jun. 2, 2003

(65) Prior Publication Data

US 2004/0219121 A1    Nov. 4, 2004

Related U.S. Application Data

(60) Provisional application No. 60/385,566, filed on Jun. 5, 2002.

(30) Foreign Application Priority Data

May 31, 2002    (FR)    ................... 02 06732

(51) Int. Cl.
*C11D 1/02* (2006.01)
*C11D 3/37* (2006.01)
*C11D 9/36* (2006.01)
*A61K 8/25* (2006.01)
*A61K 8/90* (2006.01)

(52) U.S. Cl. ................ 510/122; 510/125; 510/130; 510/426; 510/475; 510/492; 424/70.5; 424/70.11; 424/70.12; 424/70.19; 424/70.22

(58) Field of Classification Search ................ 510/122, 510/125, 130, 426, 475, 492; 424/70.5, 70.11, 424/70.12, 70.19, 70.22
See application file for complete search history.

(56) References Cited

U.S. PATENT DOCUMENTS

| | | | |
|---|---|---|---|
| 5,114,706 A | 5/1992 | Duvel | |
| 5,344,643 A | 9/1994 | Thiel et al. | |
| 5,656,257 A | 8/1997 | Fealy et al. | |
| 5,968,493 A | 10/1999 | Dornoff | |
| 6,150,313 A | 11/2000 | Harmalker et al. | |
| 6,383,994 B1 * | 5/2002 | Maurin et al. | ............... 510/119 |
| 2001/0003584 A1 | 6/2001 | Birkel et al. | |

FOREIGN PATENT DOCUMENTS

| | | |
|---|---|---|
| DE | 43 20 401 | 12/1994 |
| EP | 0 463 780 | 1/1992 |
| EP | 0 463 780 A2 | 1/1992 |
| EP | 0 566 339 | 10/1993 |
| EP | 0 818 190 | 1/1998 |
| EP | 1366746 | * 12/2003 |
| FR | 2 758 262 | 7/1998 |
| FR | 2 798 852 | 3/2001 |
| WO | 96/32092 | 10/1996 |
| WO | WO 97/33555 | 9/1997 |
| WO | WO 99/21530 | 5/1999 |
| WO | 99/38476 | 8/1999 |
| WO | 99/62493 | 12/1999 |
| WO | 00/21494 | 4/2000 |
| WO | WO 00/40628 | 7/2000 |
| WO | WO 00/71591 | 11/2000 |
| WO | WO 01/96429 | 12/2001 |

OTHER PUBLICATIONS

Patent Abstracts of Japan (in English), Kazuyuki et al, 2001-288233, Oct. 16, 2001.

* cited by examiner

*Primary Examiner*—Brian P Mruk
(74) *Attorney, Agent, or Firm*—Nixon & Vanderhye P.C.

(57) ABSTRACT

The present invention relates to a composition for washing keratinous substances, preferably keratinous fibers, comprising, in a cosmetically acceptable aqueous medium,
at least one anionic or nonionic, amphiphilic linear block copolymer comprising at least one hydrophobic block and at least one hydrophilic block, with the exception of block copolymers of ethylene oxide and of propylene oxide, block copolymers comprising urethane units and block copolymers comprising siloxane units,
at least one nonvolatile silicone, and
at least one anionic surface-active agent in combination with at least one nonionic and/or amphoteric surface-active agent, and to the use of such a composition for washing keratinous substances.

15 Claims, No Drawings

SHAMPOO COMPRISING AT LEAST ONE SILICONE AND AT LEAST ONE ANIONIC OR NONIONIC, AMPHIPHILIC LINEAR BLOCK COPOLYMER

The present application claims benefit of U.S. provisional Application No. 60/385,566, filed Jun. 5, 2002, the entire contents of which is hereby incorporated by reference.

The present invention relates to compositions for washing keratinous fibers comprising, in a base for shampoos, at least one anionic or nonionic, amphiphilic linear block copolymer, comprising at least one hydrophobic block and at least one hydrophilic block, and at least one nonvolatile silicone.

Nonvolatile silicones have been known for a long time in the cosmetics field, and in particular in the hair field, for their conditioning properties. This is because they facilitate the disentangling of the hair and confer a smooth and glossy appearance on it.

This conditioning performance of silicones, which is satisfactory on normal hair, is markedly less satisfactory, however, on hair sensitized by treatments capable of causing damage to the structure of the hair, such as oxidation dyeing or oxidation bleaching and permanent deformation. In point of fact, it is precisely hair damaged by these treatments which exhibits problems of disentangling and cosmetic flaws which would require a conditioning effect.

One approach to solving this problem consisted in combining the silicones with cationic polymers. It turned out that such a combination in fact facilitates disentangling and improves the softness of the damaged hair but the latter then becomes excessively smooth and flyaway and no longer has either body or form retention.

Furthermore, the use of silicone block copolymers, of polyurethanes comprising polyester or polyether blocks or of block copolymers comprising poly(ethylene oxide) and poly(propylene oxide) blocks, alone or in combination with silicones, has proved to be an even less satisfactory solution than those described above.

The Applicant Company has found with surprise that the use of a group of specific amphiphilic linear block copolymers in combination with at least one silicone in a specific base for shampoos makes it possible to solve the problems of the prior art. The shampoos developed by the Applicant Company facilitate the disentangling of hair in the wet state and in the dry state and give excellent cosmetic results, that is to say confer a glossy appearance and a silky feel on the hair while giving it body and form retention, this being the case both for natural hair and for moderately or highly damaged hair.

Consequently, a subject-matter of the present invention is a composition for washing keratinous substances, preferably keratinous fibers, and in particular the hair, comprising, in a cosmetically acceptable aqueous or aqueous/alcoholic medium, at least one anionic or nonionic, amphiphilic linear block copolymer comprising at least one hydrophobic block and at least one hydrophilic block, with the exception of block copolymers of ethylene oxide and of propylene oxide, block copolymers comprising urethane units and block copolymers comprising siloxane units, at least one silicone which is nonvolatile at ambient temperature, and at least one anionic surface-active agent in combination with at least one nonionic surface-active agent and/or at least one amphoteric surface-active agent.

Another subject-matter of the present invention is the use of such a composition for washing keratinous fibers.

The linear block copolymers which can be used according to the present invention are "amphiphilic" copolymers, namely copolymers comprising at least one hydrophobic block and at least one hydrophilic block.

The term "hydrophobic block" is understood to mean, according to the present invention, a block comprising at least 75 mol % of water-insoluble monomers and the term "hydrophilic block" is understood to mean a block comprising at least 75 mol % of water-soluble monomers.

The water-soluble monomers forming the hydrophilic block or blocks of the block copolymers used in the present invention can be of anionic or nonionic nature and can be used alone or in the form of a mixture comprising two or more different monomers.

Mention may be made, as examples of anionic water-soluble monomers, of carboxylic acids comprising ethylenic unsaturation, such as acrylic acid, methacrylic acid, itaconic acid, fumaric acid, crotonic acid and maleic acid, 2-acrylamido-2-methylpropanesulfonic acid, styrenesulfonic acid, vinylsulfonic acid and vinylphosphonic acid.

Nonionic water-soluble monomers encompass, inter alia, acrylamide, N—($C_{1-6}$ alkylated)acrylamides or N,N-di($C_{1-3}$ alkylated)acrylamides, polyethylene glycol acrylate, polyethylene glycol methacrylate, N-vinylacetamide, N-methyl-N-vinylacetamide, N-vinylformamide, N-methyl-N-vinylformamide, N-vinyllactams comprising a cyclic group of 4 to 9 carbon atoms, vinyl alcohol (copolymerized in the form of vinyl acetate and then hydrolyzed), ethylene oxide, hydroxyethyl acrylate, hydroxypropyl acrylate, hydroxyethyl methacrylate and hydroxypropyl methacrylate.

The water-insoluble monomers forming the hydrophobic block or blocks of the block copolymers are preferably chosen from vinylaromatic monomers, such as styrene and its alkylated derivatives, for example 4-butylstyrene, α-methylstyrene and vinyltoluene, dienes, such as butadiene and 1,3-hexadiene, and alkylated derivatives of dienes, such as isoprene and dimethylbutadiene, chloroprene, $C_{1-10}$ alkyl, $C_{6-10}$ aryl or $C_{6-10}$ aralkyl acrylates and $C_{1-10}$ alkyl, $C_{6-10}$ aryl or $C_{6-10}$ aralkyl methacrylates, such as, for example, methyl, ethyl, n-butyl, 2-ethylhexyl, tert-butyl, isobornyl, phenyl or benzyl (meth)acrylates, vinyl acetate, vinyl ethers of formula $CH_2=CH$—O—R and allyl ethers of formula $CH_2=CH$—$CH_2$—O—R where R represents a $C_{1-6}$ alkyl group, acrylonitrile, vinyl chloride, vinylidene chloride, caprolactone, ethylene, propylene, or fluorinated vinyl monomers or vinyl monomers comprising a perfluorinated chain, such as fluoroalkyl acrylates and methacrylates or alkyl α-fluoroacrylates.

As indicated above with respect to the definition of the hydrophobic and hydrophilic blocks of the amphiphilic block copolymers, the water-soluble [sic] monomers and the water-insoluble [sic] monomers represent at least 75 mol % respectively of the hydrophobic and hydrophilic blocks. In other words, the hydrophobic block or blocks can comprise up to 25 mol % of one or more water-soluble monomers. This proportion is preferably at most equal [lacuna] 10 mol % and ideally less than or equal to 5 mol %.

Similarly, the hydrophilic block or blocks can comprise up to 25 mol %, preferably up to 10 mol % and ideally up to 5 mol % of one or more water-insoluble monomers.

The linear block copolymers used also, of course, encompass those in which the hydrophilic blocks and the hydrophobic blocks are composed exclusively of water-soluble monomers and of water-insoluble monomers respectively. These blocks can be homopolymer blocks or copolymer blocks including two or more than two different monomers of the same type.

The number-average molecular mass of each block, whether hydrophobic or hydrophilic or copolymer or homopolymer, is preferably between 500 and 100 000, in particular between 500 and 50 000, with a polydispersity index ($M_w/M_n$) of between 1.01 and 3.0, preferably between 1.1 and 2.5.

The block polymers of the invention can be prepared by the synthetic processes conventionally used to produce block polymers. Mention may be made, for example, of anionic or cationic polymerizations and controlled radical polymerization (see "*New Method of Polymer Synthesis*", Blackie Academic & Professional, London, 1995, volume 2, page 1, or Trends Polym. Sci., 4, page 183 (1996) by C. J. Hawker), which controlled radical polymerization can be carried out according to different processes, such as, for example, atom transfer radical polymerization (ATRP) (see *JACS*, 117, page 5614 (1995), by Matyjasezwski et al.), or the method of radicals, such as nitroxides (Georges et al., Macromolecules, 1993, 26, 2987).

Use may also be made of these processes to produce just one of the two types of blocks of the polymer of the invention, the other block being introduced into the final polymer via the initiator used or else by a coupling reaction between the hydrophilic and hydrophobic blocks.

The washing compositions of the present invention can comprise the block copolymers in a dissolved or dispersed state and these copolymers are therefore preferably soluble or dispersible in the cosmetic medium used.

The diblock copolymers are preferably water-soluble.

The term "water-soluble" is understood to mean compounds (polymers or monomers) which, introduced into water at 25° C., and if need be neutralized, at a concentration by weight of 0.1%, make it possible to obtain a macroscopically homogeneous and transparent solution or suspension, that is to say having a light transmission value, at a wavelength of 500 nm, through a sample with a thickness of 1 cm, of least 70%, preferably of at least 80%.

As indicated above, the washing compositions of the present invention comprise—in addition to the anionic or nonionic, amphiphilic block copolymer or copolymers described above—at least one silicone which is nonvolatile at ambient temperature which is generally present at a concentration of between 0.01 and 20% with respect to the total weight of the washing composition. The term "silicone which is nonvolatile" is understood to mean, within the meaning of the present invention, any silicone with a boiling point of greater than 245° C. at atmospheric pressure.

The silicones which can be used in accordance with the invention can be soluble or insoluble in water or the composition. They are in particular polyorganosiloxanes which are insoluble in water and in the composition and which are provided in the form of silicone oils, waxes, resins and gums.

The silicones which can be used in the washing compositions may or may not be crosslinked and may or may not be organomodified.

The term "silicones which are insoluble in water and in the composition" is understood to mean those having a solubility, measured at 25° C., of less than or equal to 0.1% by weight in water or in the composition, that is to say that, above this concentration, they do not form transparent isotropic solutions.

Organopolysiloxanes are defined in more detail in the work by Walter Noll, "Chemistry and Technology of Silicones" (1968), Academic Press.

The nonvolatile silicones are preferably polyalkylsiloxanes, polyarylsiloxanes, polyalkylarylsiloxanes, silicone gums and resins, polyorganosiloxanes modified by organofunctional groups, and their mixtures.

These silicones are chosen more particularly from polyalkylsiloxanes, among which may mainly be mentioned polydimethylsiloxanes comprising trimethylsilyl end groups having a viscosity of $5 \times 10^{-6}$ to 2.5 m²/s at 25° C. and preferably $1 \times 10^{-5}$ to 1 m²/s.

Mention may be made, among these polyalkylsiloxanes, without implied limitation, of the following commercial products:

Silbione® oils of the 47 and 70 047 series or Mirasil® oils sold by Rhône-Poulenc, such as, for example, the oil 70 047 V 500 000;

oils of the Mirasil® series sold by Rhône-Poulenc;

oils of the 200 series from Dow Corning, such as more particularly DC200 with a viscosity of 60 000 cSt;

Viscasil® oils from General Electric and some oils of the SF series (SF 96, SF 18) from General Electric.

Mention may also be made of polydimethylsiloxanes comprising dimethylsilanol end groups (dimethiconol according to the CTFA name), such as the oils of the 48 series from Rhône-Poulenc.

Mention may also be made, in this class of polyalkylsiloxanes, of the products sold under the names "Abil Wax 9800 and 9801" by Goldschmidt, which are poly($C_1$–$C_{20}$) alkylsiloxanes.

The polyalkylarylsiloxanes are chosen particularly from linear and/or branched polydimethylmethylphenylsiloxanes or polydimethyldiphenylsiloxanes with a viscosity of $1 \times 10^{-5}$ to $5 \times 10^{-2}$ m²/s at 25° C.

Mention may be made, among these polyalkylarylsiloxanes, as examples, of the products sold under the following names:

Silbione® oils of the 70 641 series from Rhône-Poulenc;

oils of the Rhodorsil® 70 633 and 763 series from Rhône-Poulenc;

the oil Dow Corning 556 Cosmetic Grade Fluid from Dow Corning;

silicones of the PK series from Bayer, such as the product PK20;

silicones of the PN or PH series from Bayer, such as the products PN1000 and PH1000;

some oils of the SF series from General Electric, such as SF 1023, SF 1154, SF 1250 or SF 1265.

The silicone gums which can be used in accordance with the invention are in particular polydiorganosiloxanes having high number-average molecular masses of between 200 000 and 1 000 000 which are used alone or as a mixture in a solvent. This solvent can be chosen from silicones of volatile nature, polydimethylsiloxane (PDMS) oils, polyphenylmethylsiloxane (PPMS) oils, isoparaffins, polyisobutylenes, methylene chloride, pentane, dodecane, tridecanes or their mixtures.

Mention may more particularly be made of the following products:

polydimethylsiloxane, polydimethylsiloxane/methylvinylsiloxane gums, polydimethylsiloxane/diphenylmethylsiloxane, polydimethylsiloxane/phenylmethylsiloxane, polydimethylsiloxane/diphenylsiloxane/methylvinylsiloxane.

Products which can more particularly be used in accordance with the invention are mixtures, such as:

mixtures formed from a polydimethylsiloxane hydroxylated at the chain end (named dimethiconol according to the nomenclature of the CTFA dictionary) and from a cyclic polydimethylsiloxane (named cyclomethicone according to the nomenclature of the CTFA dictionary), such as the product Q2 1401 sold by Dow Corning;

mixtures formed from a polydimethylsiloxane gum with a cyclic silicone, such as the product SF 1214 Silicone Fluid from General Electric; this product is a gum SF 30, corresponding to dimethicone having a number-average molecular weight of 500 000, dissolved in the oil SF 1202 Silicone Fluid, corresponding to decamethylcyclopentasiloxane;

mixtures of two PDMSs with different viscosities and more particularly of a PDMS gum and of a PDMS oil, such as the product SF 1236 from General Electric. The product SF 1236 is the mixture of a gum SE 30 defined above, having a viscosity of 20 $m^2/s$, and of an oil SF 96, with a viscosity of $5 \times 10^{-6}$ $m^2/s$. This product preferably comprises 15% of gum SE 30 and 85% of an oil SF 96.

The organopolysiloxane resins which can be used in accordance with the invention are crosslinked siloxane systems including the units:

$R_2SiO_{2/2}$, $R_3SiO_{1/2}$, $RSiO_{3/2}$ and $SiO_{4/2}$, in which R represents a hydrocarbonaceous group having 1 to 16 carbon atoms or a phenyl group. Those which are particularly preferred among these products are those in which R denotes a lower $C_1$–$C_4$ alkyl radical, more particularly methyl, or a phenyl radical.

Mention may be made, among these resins, of the product sold under the name "Dow Corning 593" or those sold under the names "Silicone Fluid SS 4230 and SS 4267" by General Electric and which are silicones with a dimethyl/trimethylsiloxane structure.

Mention may also be made of resins of the trimethylsiloxysilicate type sold in particular under the names X22-4914, X21-5034 and X21-5037 by Shin-Etsu.

The organomodified silicones which can be used in accordance with the invention are silicones as defined above comprising, in their structure, one or more organofunctional groups attached via a hydrocarbonaceous radical.

Mention may be made, among organomodified silicones, of the polyorganosiloxanes comprising:

polyethyleneoxy and/or polypropyleneoxy groups optionally comprising $C_6$–$C_{24}$ alkyl groups, such as the products named dimethicone copolyol sold by Dow Corning under the name DC 1248 or the oils Silwet L 722, L 7500, L 77 or L 711 from Union Carbide and the ($C_{12}$)alkyl methicone copolyol sold by Dow Corning under the name Q2 5200;

substituted or unsubstituted aminated groups, such as the products sold under the name [sic] GP 4 Silicone Fluid and GP 7100 by Genesee or the products sold under the names Q2 8220 and Dow Corning 929 or 939 by Dow Corning. The substituted aminated groups are in particular $C_1$–$C_4$ aminoalkyl groups;

thiol groups, such as the products sold under the names "GP 72 A" and "GP 71" from Genesee;

alkoxylated groups, such as the product [sic] sold under the name [sic] "Silicone Copolymer F-755" by SWS Silicones and Abil Wax 2428, 2434 and 2440 by Goldschmidt;

hydroxylated groups, such as the polyorganosiloxanes comprising a hydroxyalkyl functional group disclosed in French Patent Application FR-A-85 16334 corresponding to the formula (V):

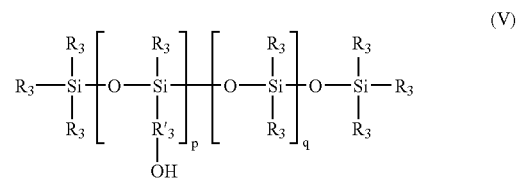

(V)

in which the $R_3$ radicals, which are identical or different, are chosen from methyl and phenyl radicals; at least 60 mol % of the $R_3$ radicals denoting methyl; the $R'_3$ radical is a divalent hydrocarbonaceous $C_2$–$C_{18}$ alkylene link; p is between 1 and 30 inclusive; and q is between 1 and 150 inclusive;

acyloxyalkyl groups, such as, for example, the polyorganosiloxanes disclosed in French Patent Application FR-A-2 641 185 and corresponding to the formula (VI):

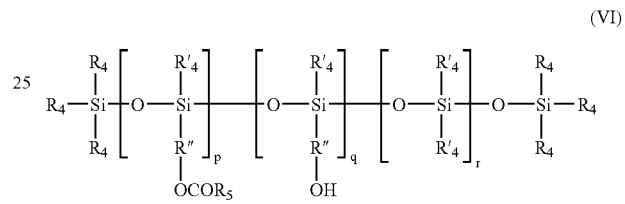

(VI)

in which:

$R_4$ denotes a methyl, phenyl, —$OCOR_5$ or hydroxyl group, only one of the $R_4$ radicals per silicon atom being able to be OH;

each $R'_4$ denotes a methyl or phenyl group; at least 60% as a molar proportion of the combined radicals $R_4$ and $R_{14}$ denoting a methyl group;

$R_5$ denotes a $C_8$–$C_{20}$ alkyl or alkenyl group;

R" denotes a divalent, linear or branched, hydrocarbonaceous $C_2$–$C_{18}$ alkylene radical;

r is between 1 and 120 inclusive;

p is between 1 and 30;

q is equal to 0 or is less than 0.5p, p+q being between 1 and 30; the polyorganosiloxanes of formula (VI) can comprise:

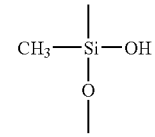

groups in proportions not exceeding 15% of the sum p+q+r.

The compounds of formula (VI) can be prepared by esterification of polyorganosiloxanes comprising a hydroxyalkyl functional group of formula (V) above.

anionic groups of the carboxyl type, such as, for example, in the products disclosed in Patent EP 186 507 from Chisso Corporation, or of alkylcarboxyl type, such as those present in the product X-22-3701E from Shin-Etsu; 2-hydroxyalkylsulfonate type; or 2-hydroxyalkylthiosulfate type, such as the products sold by Goldschmidt under the names "Abil S201" and "Abil S255";

hydroxyacylamino groups, such as the polyorganosiloxanes disclosed in Application EP 342 834. Mention may be made, for example, of the product Q2-8413 from Dow Corning.

According to the invention, it is also possible to use silicones comprising a polysiloxane portion and a portion composed of a non-silicone organic chain, one of the two portions constituting the main chain of the polymer [lacuna] the other being grafted to the said main chain. These polymers are disclosed, for example, in Patent Applications EP-A-412 704, EP-A-412 707, EP-A-640 105 and WO 95/00578, EP-A-582 152 and WO 93/23009, and Patents U.S. Pat. No. 4,693,935, U.S. Pat. No. 4,728,571 and U.S. Pat. No. 4,972,037. These polymers are preferably anionic or nonionic polymers.

Such polymers are, for example, the copolymers capable of being obtained by radical polymerization starting from the mixture of monomers composed of:
  a) 50 to 90% by weight of tert-butyl acrylate;
  b) 0 to 40% by weight of acrylic acid;
  c) 5 to 40% by weight of silicone macromer of formula:

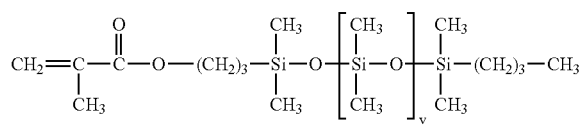

with v being a number ranging from 5 to 700; the percentages by weight being calculated with respect to the total weight of the monomers.

Other examples of grafted silicone polymers are in particular polydimethylsiloxanes (PDMSs) to which are grafted, via a connecting link of thiopropylene type, mixed polymer units of the poly((meth)acrylic acid) type and of the poly(alkyl(meth)acrylate) type and polydimethylsiloxanes (PDMSs) to which are grafted, via a connecting link of thiopropylene type, polymer units of the poly(isobutyl (meth)acrylate) type.

According to the invention, all the silicones can also be used in the form of emulsions.

The silicones which are particularly preferred in accordance with the invention are:
  polydimethylsiloxane oils or gums,
  polysiloxanes comprising aminated groups, such as amodimethicones or trimethylsilylamodimethicones.

The combination of the two types of polymers essential for the present invention described above (silicone+ block copolymer) is found in a specific base for shampoos comprising the combination of at least one anionic surface-active agent and of at least one nonionic surface-active agent and/or of at least one amphoteric surface-active agent.

The anionic, nonionic and amphoteric surface-active agents which can be used in the washing compositions of the present invention are known and commonly used in the cosmetics field.

Mention may in particular be made, as anionic surface-active agents which can be used in the present invention, of salts, in particular alkali metal salts, such as sodium salts, ammonium salts, amine salts, aminoalcohol salts or alkaline earth metal salts, for example magnesium salts, of the following types: alkyl sulfates, alkyl ether sulfates, alkylamido ether sulfates, alkylarylpolyether sulfates, monoglyceride sulfates; alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acylsarcosinates and acylglutamates, the alkyl and acyl groups of all these compounds comprising from 6 to 24 carbon atoms and the aryl group preferably denoting a phenyl or benzyl group.

Use may be also be made of $C_{6-24}$ alkyl monoesters of polyglycosidedicarboxylic acids, such as alkyl glucosidecitrates, alkyl polyglycosidetartrates and alkyl polyglycosidesulfosuccinates, alkyl sulfosuccinamates, acylisethionates and N-acyltaurates, the alkyl or acyl group of all these compounds comprising from 12 to 20 carbon atoms.

Another group of anionic surface-active agents which can be used in the compositions of the present invention is that of the acyllactylates, the acyl group of which comprises from 8 to 20 carbon atoms.

In addition, mention may also be made of alkyl-D-galactosideuronic acids and their salts, and polyoxyalkylenated $(C_{6-24})$alkyl ether carboxylic acids, polyoxyalkylenated $(C_{6-24})$alkyl$(C_{6-24})$aryl ether carboxylic acids, polyoxyalkylenated $(C_{6-24})$alkylamido ether carboxylic acids and their salts, in particular those comprising from 2 to 50 ethylene oxide units, and their mixtures.

Use is preferably made of alkyl sulfates, alkyl ether sulfates and alkyl ether carboxylates, and their mixtures, in particular in the form of alkali metal or alkaline earth metal, ammonium, amine or aminoalcohol salts.

The amphoteric surface-active agents which can be used in the present invention can in particular be derivatives of aliphatic secondary or tertiary amines in which the aliphatic group is a linear or branched chain comprising from 8 to 22 carbon atoms and comprising at least one anionic group, such as, for example, a carboxylate, sulfonate, sulfate, phosphate or phosphonate group. Mention may in particular be made of $(C_{8-20})$alkyl betaines, sulfobetaines, $(C_{8-20})$alkyl amido-$(C_{6-8})$alkyl betaines or $(C_{8-20})$alkyl amido$(C_{6-8})$alkyl sulfobetaines.

Mention may be made, among the amine derivatives, of the products sold under the name Miranol®, as disclosed in patents U.S. Pat. No. 2,528,378 and U.S. Pat. No. 2,781,354 and classified in the CTFA dictionary, 3rd edition, 1982, under the names Amphocarboxyglycinate and Amphocarboxypropionate, with the respective structures (1) and (2):

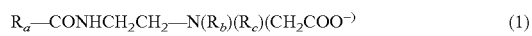

in which:
  $R_a$ represents an alkyl group derived from an acid $R_a$—COOH present in hydrolyzed coconut oil, or a heptyl, nonyl or undecyl group,
  $R_b$ represents a β-hydroxyethyl group, and
  $R_c$ represents a carboxymethyl group; and

in which:
  B represents —$CH_2CH_2OX'$,
  C represents —$(CH_2)_z$—Y', with z=1 or 2,
  X' represents the —$CH_2CH_2$—COOH group or a hydrogen atom,
  Y' represents —COOH or the —$CH_2$—CHOH—$SO_3$H group,
  $R_a'$ represents an alkyl group of an acid $R_a'$—COOH present in hydrolyzed linseed oil or coconut oil, an alkyl group, in particular a $C_{1-7}$ alkyl group and its iso form, or an unsaturated $C_{17}$ group.

These compounds are classified in the CTFA dictionary, 5th edition, 1993, under the names disodium cocoamphodiacetate, disodium lauroampho-diacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

Mention may be made, by way of example, of the cocoamphodiacetate sold by Rhodia under the tradename Miranol® C2M concentrate.

Use is preferably made, among amphoteric surfactants, of ($C_{8-20}$ alkyl) betaines, ($C_{8-20}$ alkyl)amido($C_{6-8}$ alkyl) betaines, alkylamphodiacetates and their mixtures.

The nonionic surfactants which can be used in the compositions of the present invention are compounds well known per se (see in particular in this respect "Handbook of Surfactants" by M. R. Porter, published by Blackie & Son (Glasgow and London), 1991, pp. 116–178). They are chosen in particular from polyethoxylated, polypropoxylated or polyglycerolated fatty acids, ($C_{1-20}$)alkylphenols, α-diols or alcohols having a fatty chain comprising, for example, from 8 to 18 carbon atoms, it being possible for the number of ethylene oxide or propylene oxide groups to range in particular from 2 to 50 and it being possible for the number of glycerol groups to range in particular from 2 to 30.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5 glycerol groups and in particular from 1.5 to 4, sorbitan ethoxylated fatty acid esters having from 2 to 30 ethylene oxide units, sucrose fatty acid esters, polyethylene glycol esters of fatty acids, ($C_{6-24}$ alkyl)polyglycosides, N—($C_{6-24}$ alkyl)glucamine derivatives, or amine oxides, such as oxides of ($C_{10-14}$ alkyl) amines or N—($C_{10-14}$ acyl)aminopropylmorpholine oxides.

Use is preferably made, among the abovementioned nonionic surfactants, of ($C_{6-24}$ alkyl)polyglycosides.

The amount of anionic surface-active agents is preferably between 3% and 35% by weight, in particular between 5% and 25% by weight, with respect to the total weight of the cosmetic composition.

The total amount of amphoteric and/or nonionic surface-active agents is preferably between 0.5 and 30% and in particular between 1 and 20% with respect to the total weight of the composition.

The pH of the compositions of the present invention is preferably between 2 and 11 and in particular between 3 and 10.

The liquid medium of the compositions of the invention is aqueous or aqueous/alcoholic, that is to say that, in the latter case, the compositions comprise, in addition to an aqueous phase, one or more solvents chosen from lower alcohols, such as ethanol or isopropanol, and polyols, such as glycerol, propylene glycol and polyethylene glycols.

The compositions according to the invention can also comprise cosmetic active principles or formulation additives, such as anionic, nonionic, cationic or amphoteric film-forming polymers, natural or synthetic, anionic, amphoteric, zwitterionic, nonionic or cationic and associative or nonassociative polymeric thickeners, nonpolymeric thickeners, such as acids or electrolytes, cationic surface-active agents, pearlescence agents, opacifying agents, dyes or pigments, fragrances, mineral, vegetable and/or synthetic oils, waxes, including ceramides, vitamins, UV screening agents, antidandruff agents, agents for combating free radicals, plasticizers, preservatives or pH-stabilizing agents.

A person skilled in the art will take care to choose the optional additives and their amount [sic] so that they do not harm the advantageous properties of the compositions for washing keratinous fibers of the present invention.

The invention is illustrated using the following example.

EXAMPLE 1

The following three shampoos are prepared (percentages of active materials):

|  | A (according to the invention) | B (comparative) | C (comparative) |
|---|---|---|---|
| Anionic surface-active agent[a] | 17% | 17% | 17% |
| Amphoteric surface-active agent[b] | 2.5% | 2.5% | 2.5% |
| PS-b-PEO diblock copolymer[c] | 0.5% | — | — |
| PEO-b-PPO diblock copolymer[d] | — | — | 0.5% |
| Amodimethicone[e] | 1% | 1% | 1% |
| Water | q.s. for 100% | q.s. for 100% | q.s. for 100% |

[a] sodium lauryl ether sulfate (2 EO)
[b] cocoylbetaine
[c] poly(styrene-b-ethylene oxide) diblock copolymer sold under the name Tegomer® SE 1010 by Goldschmidt
[d] poly(ethylene oxide-b-propylene oxide) block copolymer sold under the name Synperonic PE/F127 by ICI
[e] DC 939, Dow Chemical Each of these shampoos is tested on a lock of sensitized hair having an alkaline solubility of 20%. Each lock is evaluated, after drying, by a group of ten experts.

Ten experts out of ten find that the lock washed with the shampoo of the invention (Composition A) and dried is more coated, smoother and glossier than that washed with Composition B (comparative) which does not comprise diblock block polymer but only a silicone.

Nine experts out of ten found that the lock washed with the shampoo of the invention (Composition A) and dried is softer, glossier and smoother than that washed with Composition C comprising a silicone in combination with a nonionic diblock copolymer of the prior art.

What is claimed is:

1. A composition for washing keratinous substances, comprising, in a cosmetically acceptable aqueous or aqueous/alcoholic medium,
   at least one anionic or nonionic, amphiphilic linear block copolymer comprising at least one hydrophobic block and at least one hydrophilic block, with the exception of block copolymers of ethylene oxide and of propylene oxide, block copolymers comprising urethane units and block copolymers comprising siloxane units,
   at least one silicone which is nonvolatile at ambient temperature, and
   at least one anionic surface-active agent in combination with at least one nonionic surface-active agent and/or at least one amphoteric surface-active agent,
   wherein the hydrophilic block of the amphiphilic linear block copolymer are formed of water-soluble monomers chosen from anionic water-soluble monomers, nonionic water-soluble monomers or a mixture of these,
   said anionic water-soluble monomers being selected from carboxylic acids comprising ethylenic unsaturation, 2-acrylamido-2-methylpropanesulphonic acid, styrenesulphonic acid, vinylsulphonic acid and vinylphosphonic acid, said nonionic water-soluble monomers being selected from acrylamide, N-($C_{1-6}$ alkylated)acrylamides or N,N-di($C_{1-3}$ alkylated)acrylamides, polyethylene glycol acrylate, polyethylene glycol methacrylate, N-vinylacetamide, N-methyl-N-vinylacetamide, N-vinylformamide, N-methyl-N-vinylformamide, N-vinyllactams comprising a cyclic group of 4 to 9 carbon atoms, vinyl alcohol, ethylene oxide, hydroxyethyl acrylate, hydroxypropyl acrylate, hydroxyethyl methacrylate and hydroxypropyl methacrylate, and said hydroohobic block being formed of water-insoluble monomers chosen from vinylaromatic monomers, dienes and alkylated derivatives of dienes, chloroprene, $C_{1-10}$ alkyl, $C_{6-10}$ aryl or $C_{1-10}$ aralkyl acrylates, $C_{1-10}$ alkyl, $C_{6-10}$ aryl or $C_{1-10}$ aralkyl methacrylates, vinyl acetate, vinyl ethers of formula $CH_2=CH-O-R$ and allyl ethers of formula $CH_2=CH-CH_2-O-R$ where R represents a $C_{1-6}$ alkyl group, acrylonitrile, vinyl chloride, vinylidene chloride, caprolactone, ethylene, propylene and fluorinated vinyl monomers or vinyl monomers comprising a perfluorinated chain.

2. The washing composition as claimed in claim 1, wherein the amphiphilic linear block copolymer is dissolved or dispersed in the aqueous or aqueous/alcoholic medium.

3. The washing composition as claimed in claim 2, wherein the amphiphilic linear block copolymer is soluble in water.

4. The washing composition as claimed in claim 1, wherein the hydrophilic block or blocks comprise up to 25 mol %, of one or more of the water-insoluble monomers.

5. The washing composition as claimed in claim 1, wherein the hydrophobic block or blocks comprise up to 25 mol %, of one or more of the water-soluble monomers.

6. The washing composition as claimed in claim 1, wherein the amphiphilic block copolymer or copolymers are present at a concentration ranging from 0.01 to 20%, with respect to the total weight of the washing composition.

7. The washing as claimed in claim 1, wherein the nonvolatile silicone or silicones are chosen from silicone oils, waxes, resins and gums which may or may not be crosslinked and which may or may not be organomodified.

8. The washing composition as claimed in claim 1, wherein the nonvolatile silicone or silicones are present at a concentration of between 0.01 and 20% with respect to the total weight of the washing composition.

9. The washing composition as claimed in claim 1, wherein the anionic surface-active gent or agents are chosen from alkyl sulphates, alkyl ether sulphates and alkyl ether carboxylates, and their mixtures, in particular in the form of alkali metal or alkaline earth metal, ammonium, amine or aminoalcohol salts.

10. The washing composition as claimed in claim 1, wherein the concentration of anionic surface-active agents is between 3 and 35% by weight, with respect to the total weight of the composition.

11. The washing composition as claimed in claim 1, wherein the nonionic surface-active agent is a ($C_{6-24}$ alkyl) polyglycoside.

12. The washing composition as claimed in claim 1, wherein the amphoteric surface-active agent is chosen from ($C_{8-20}$ alkyl) betaines, ($C_{8-20}$ alkyl) amido($C_{6-8}$ alkyl) betaines, alkylamphodiacetates and their mixtures.

13. The washing composition as claimed in claim 1, wherein the total amount of amphoteric and/or nonionic surface-active agents is between 0.5 and 30% with respect to the total weight of the composition.

14. A method of washing keratinous fibers comprising applying the composition of claim 1 to said fibers.

15. The washing composition as claimed in claim 1, wherein the total amount of amphoteric and/or nonionic surface-active agents is between 1 and 20% with respect to the total weight of the composition.

* * * * *